United States Patent [19]

Weyl et al.

[11] 3,960,692

[45] June 1, 1976

[54] ELECTRO-CHEMICAL SENSOR CONSTRUCTION

[75] Inventors: Helmut Weyl, Schwieberdingen; Bodo Ziegler, Stuttgart, both of Germany

[73] Assignee: Robert Bosch G.m.b.H., Gerlingen-Schillerhohe, Germany

[22] Filed: July 29, 1974

[21] Appl. No.: 492,520

[30] Foreign Application Priority Data
Oct. 6, 1973 Germany............................ 2350252

[52] U.S. Cl............................. 204/195 S; 123/119 E
[51] Int. Cl.$^2$......................................... G01N 27/46
[58] Field of Search........................ 204/1 T, 195 S

[56] References Cited
UNITED STATES PATENTS

| | | | |
|---|---|---|---|
| 3,454,486 | 7/1969 | Davies | 204/195 S |
| 3,468,780 | 9/1969 | Fischer | 204/195 S |
| 3,481,855 | 12/1969 | Kolodney et al. | 204/195 S |
| 3,546,086 | 12/1970 | Sayles | 204/195 S |
| 3,711,394 | 1/1973 | Minushkin et al. | 204/195 S |
| 3,841,987 | 10/1974 | Friese et al. | 204/195 S |

FOREIGN PATENTS OR APPLICATIONS
21,673   8/1961   Germany.................... 204/195 S

*Primary Examiner*—T. Tung
*Attorney, Agent, or Firm*—Flynn and Frishauf

[57] ABSTRACT

To provide for mechanical isolation between the connection to the interior of a solid electrolyte material, such as zirconium dioxide, used in an oxygen ion concentration cell, for example to sense the composition of exhaust gases from an internal combustion engines, an electrical connection element which may be a metal cap, a cup-shaped element, or a resilient electrically conductive mass such as granular material, graphite, copper powder, or the like, is conductively arranged with respect to at least one of the conductor strips or paths connected to the solid electrolyte body, and an axially extending spiral compression spring is interposed between an electrical contact terminal and the connection element to provide for resilient, yielding connection between the terminal and the conductive paths, and avoid placing of stresses on the solid electrolyte body during manufacture thereof.

14 Claims, 4 Drawing Figures

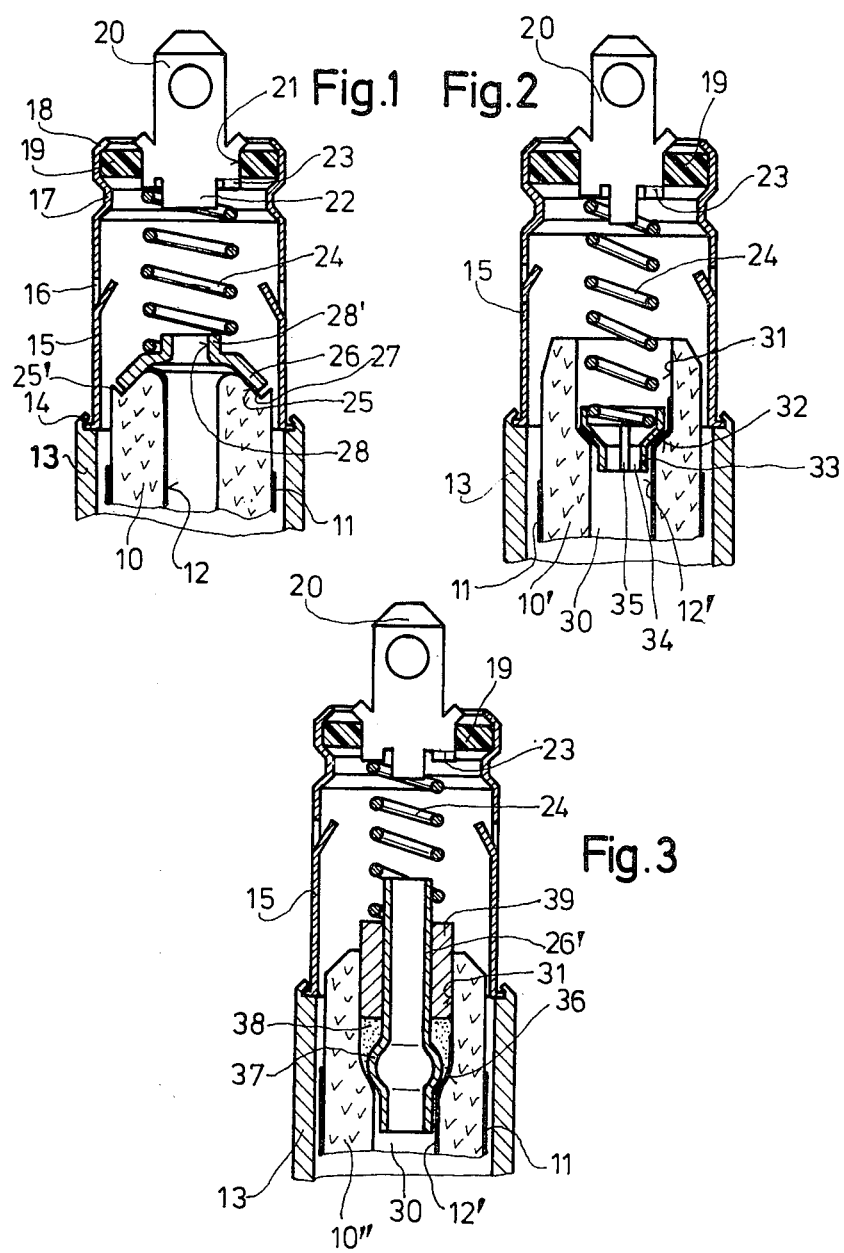

ELECTRO-CHEMICAL SENSOR CONSTRUCTION

The present invention relates to an electrochemical sensor to obtain an electrical output signal in dependence on the composition of gases to which it is exposed, and more particularly to determine oxygen content in the exhaust gases from internal combustion engines used in automotive vehicles.

Sensors of this type have previously been proposed; briefly, they include an ion conductive solid electrolyte tube which is closed at one end. The outside of the tube has an electron conductive catalyzing layer applied thereto, the catalyzing layer being electrically connected to the housing of the sensor which, typically, is then electrically connected to chassis or ground of the vehicle. This side is the one which is exposed to exhaust gases when the sensor is used as an exhaust gas sensing device. The inside of the closed tube is exposed to ambient atmosphere and has a conductive strip or layer applied thereto which extends as far as the closed, inner end. The outer portion of the conductor has an electrical connection which ends in a terminal, adapted for electrical and mechanical connection to a standard connector terminal. The present invention is particularly related to the arrangement which effects the electrical connection.

It has previously been proposed to provide a conductive strip or path at the inside of the solid electrolyte tube, to be then electrically connected to the terminal. The free end of the tube is formed with a push-type terminal which is connected to the free end by hard-soldering, brazing, attachment in a conductive glass melt, forming a glass socket, or by clamping the solid electrolyte tube in a counter-sunk recess. Manufacture of such sensors, with sockets of this type, is difficult. Damage to the conductor, the solid electrolyte tube, or the socket is frequent during manufacture. The socket connector is customarily inserted in an insulating disk, which also may serve as a support for a protective tube or shell for the sensor. During manufacture, that is, attachment of the tube, the insulating disk, and the like, it is difficult to avoid transfer of stresses to the solid electrolyte tube, for example stresses arising when a glass melt is inserted which later lead to malfunction of the sensor itself. To avoid such difficulties, it has previously been proposed to manufacture sensors in which the actual terminal flag, or terminal lug is connected to the inner sensor conductor by a supple resilient connecting conductor, such as a pigtail, or the like. It has been found, however, that this is not an entirely satisfactory solution either.

It is an object of the present invention to provide a sensor, and more particularly a sensor having a connecting arrangement which is simple to manufacture, and in which the electrical connection as well as the mechanical attachment of the solid electrolyte do not introduce mechanical stresses to the solid electrolyte tube during manufacture.

Subject matter of the present invention: Briefly, the contacting element, that is, typically a terminal lug or terminal flag is secured in an insulating disk, directly or indirectly attached to the housing of the sensor. The conductor at the inside of the sensor tube and the terminal flag are electrically connected by means of an axially extending spiral compression spring, directly or indirectly bearing on the inner conductor path.

The structure, in accordance with the invention, relieves stresses during manufacture which might be placed on the solid electrolyte tube, since the spring absorbs any stresses which might be applied thereto, and which may be transferred from the attachment flag or lug.

In accordance with a feature of the invention, the internal conductor path is so arranged that it covers an edge surface of the solid electrolyte tube, which is preferably formed in frusto-conical shape. A pressure washer, of electrically conductive material and preferably shaped to conform to the frusto-conical shape of the end surface of the tube is placed thereagainst, maintained in contact with the end surface by a spiral compression spring. Various other constructional arrangements are possible; in accordance with another feature of the invention which results in a structure particularly simple to assemble, the solid electrolyte tube is formed with a counter-sink bore of somewhat enlarged diameter to form an internal shoulder. A pot-shaped element is inserted in the bore, seating in the shoulder, and made of electrically conductive material, and a spiral compression spring biasses the pot-shaped insert against the conductive path which extends into the counter-sink bore.

In accordance with another feature of the invention, and one in which frictional abrasion due to vibration of the sensor, and possible rubbing contact of any element is essentially inhibited, a sealing mass is used formed of a resilient, electrically conductive substance; the solid electrolyte body is formed, again, with a counter-sink bore to form a shoulder into which a connecting element extends, seating against the shoulder, and on which, for example by means of conductive washers, a sealing mass is retained, compressed against the inside of the hollow electrolyte body. Such a sealing mass may, for example, be a fine granulate of conductive material, such as copper powder, graphite powder, or a resilient, yielding conductive element, such as dispersions of conductive particles in a resilient binder. The resilient mass, be it a granulate, or a resilient element, is compressed and yieldingly urged against the inner surface of the tube by the spring, compressing the material. Possible rubbing contact between a connecting element and the conductive path is avoided.

The invention will be described by way of example with reference to the accompanying drawings, wherein:

FIG. 1 is a longitudinal sectional view through the terminal end of an exhaust gas sensor, to an enlarged scale, in which the end surface of the sensor is frusto-conical and a metal cap fits against the conductor path;

FIG. 2 is a longitudinal sectional view, to an enlarged scale, similar to FIG. 1 and showing another embodiment of the invention, utilizing an insert fitting against a counter-sunk bore;

Figure 4:
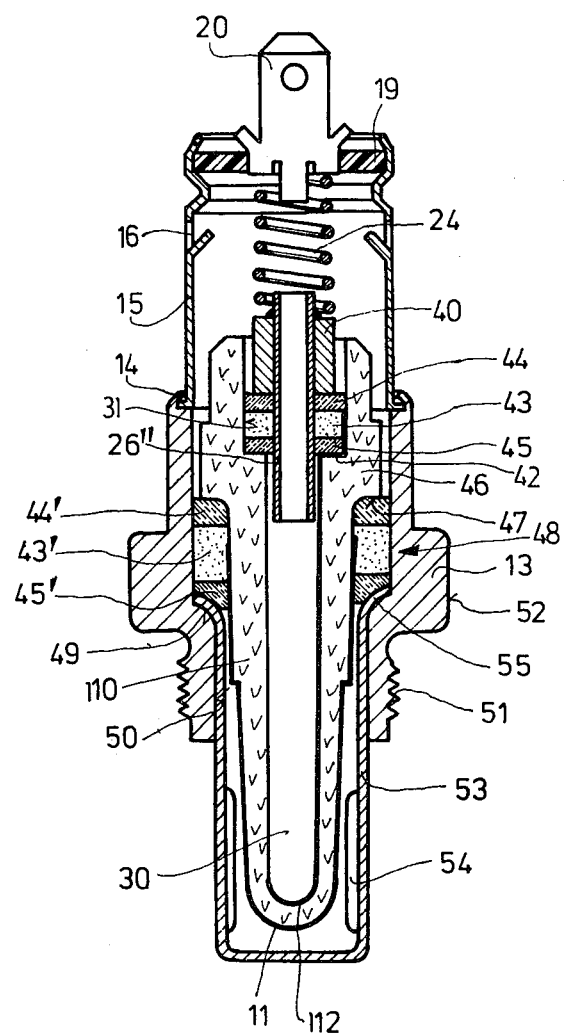

FIG. 3 is a view similar to FIG. 1 and showing another embodiment in which an insert with an outwardly projecting bulge retains an electrically conductive sealing mass within a counter-sunk bore of the sensor; and FIG. 4 illustrates, highly schematically, and in cross section, to an enlarged scale, another embodiment of a sensor in which a resilient electrically conductive sealing mass is located in a counter-sink of the sensor and the electrolytic tube is retained at the outside thereof also by a similar electrically conductive resilient mass.

Embodiment of FIG. 1: The electro-chemical sensor is an oxygen ion concentration cell having an ion conductive solid electrolyte; such cells are known and used, for example, to sense the oxygen content in the exhaust gases from internal combustion engines. The sensing element is made of a tube 10 which is a solid electrolyte, closed at one end, and made of cubic zirconium dioxide. The outside surface of the solid electrolyte tube is coated with a catalyzing layer 11, for example platinum, forming simultaneously a conductor for an electrical connection. At the inside of the solid electrolyte body 10, a conductive path 12, preferably also platinum, is provided. A housing 13 is provided in which the solid electrolyte tube 10 is secured, housing 13 being metallic and forming one terminal of the sensor, by connection to the platinum layer 11 (as will appear). The inner end surface of the sensor has an electrical terminal conductor flag or lug 20, which is electrically connected to the inner platinum conductor 12. A protective tube or sleeve 15, having openings 16 punched therein to provide for access of air in the interior thereof is connected to housing 13, for example by peening the housing 13 over a projecting rim or edge 14 of sleeve 13. Sleeve 15 is further formed with an inwardly drawn ring 17, and an overlying ring 18; an insulating disk 19, for example formed of fiber-board, plastic or other suitable insulating material is retained between the inwardly drawn ring 17 and the overlying edge 18, so that the insulating disk 19 is securely retained on the sleeve 15. The insulating disk 19 is formed with a slit 21 through which a contacting flag or lug 20 is carried; flag 20 is secured to disk 19 by an extended portion 21 which is deformed at its outer and inner ends to be seated securely within slit 21. The inner end of the deformation of the lug 20 forms a shoulder 23 against which a spiral compression spring 24 can bear, spring 24 being in electrical as well as mechanical contact with shoulder 23 and retained, in centered position, by the central extension 22 of lug 20.

The inner conductive path 12, in accordance with a feature of the present invention, is connected to lug 20 electrically by means of the spring 24. The conductive path 12 is carried around the facing edge of the solid electrolyte tube 10, that is, over the end face 25 which, preferably, is formed in generally frusto-conical shape, with rounded edges, as seen in FIG. 1. A connecting cap 26, with a conical portion fits over the conical portion of the end surface 25 of tube 10, and hence against the conductive path 12. The conical cap 26 is of electrically conductive material and has an inner conductive surface 27 in electrical contact with path 12. Disk 26 has a central hole 28, surrounded by an upstanding sleeve-like portion 28'. Hole 28 permits air to pass through the openings 16 into the interior of the closed tube formed by the solid electrolyte body 10. The cap 26 is held in electrical contact with path 12 by the bias pressure of spring 24. The cap 26 is retained in centered position on the body 10 by the fitting surfaces 25, 27; additionally, the body 10 may be formed at its end surface with a slightly upstanding lip 25', spaced slightly from the ends of cap 26, when cap 26 is centered, to further assist in proper centering and maintenance of respective positional relationships between the body 10 and the cap 26. The cap 26 cannot, therefore, shift on the surface 25; the spring 24, itself, is centered around the central sleeve portion 28 of cap 26 as well as by the central portion 22 of the lug 20.

The outside seal, attachment, and electrical contact between the outer surface of the solid electrolyte body 10 and housing 13 may be conventional; the body 10 may be inserted in the housing 13, for example, by an electrically conductive glass melt, by brazing, hard-soldering, or by a resilient, yielding electrically conductive sealing mass.

Embodiment of FIG. 2: The general construction is similar to that of FIG. 1 and in this embodiment, as in the others, similar parts have been given the same reference numerals and will not be described again. The hollow space 30 in the center of the solid electrolyte body is formed with a counter-sink bore 31, forming an internal shoulder 32. The electrical conductor 12' extends into the counter-sink bore, over the shoulder 32. A pot-shaped insert 33, for example made of nickel, forms the connecting element against which compression spring 24 will bear. The pot-shaped element 33 is centrally open, to permit air to pass to the inside hollow portion 30 of the solid electrolyte body 10. The open end is seen at 34. To compensate for mechanical stress, the pot-shaped element 33 is not circumferentially closed, but rather is formed with a longitudinal slit 35, to permit expansion and contraction thereof. The pot-shaped element 33 can be coated with a thin layer of gold or platinum in order to increase its resistance to oxidation. Compression spring 25 fits against the expanded portion of the pot-shaped element 33 and is compressed against the shoulder 23 of the connecting lug 20.

The solid electrolyte tube 10 is secured to the housing 13, and electrically connected in conventional manner, as described in connection with FIG. 1.

Embodiment of FIG. 3: The solid electrolyte body 10" with the inner electrically conductive path 12", which may be a platinum strip, is formed with a counter-sink bore 31". The shoulder 36 formed by the counter-sink bore is gradual; a conically shaped bulge 37 is formed in a tube 26' forming the connecting element; a yielding, resilient, electrically conductive mass 38 is located above the bulge 37. This mass may be, for example, a conductive granulate, such as graphite powder, copper powder, or the like. A compression sleeve 39 surrounds the tube 26', compressing the conductive granulate 38. Spring 24 bears against sleeve 39 to form the electrical connection between conductive path 12", to the mass 38, and hence to the central sleeve 26' and the sleeve 39, then over spring 24 to shoulder 23 of lug 20.

Embodiment of FIG. 4: A metallic connecting portion 26" is separated from contact with the solid electrolyte body 110 by a resilient, yielding mass of electrically conductive material 43. This has the advantage that there is no direct unyielding, metallic contact between the central connecting element 26" and the conductor, or conductive path 112 on the inside of the solid electrolyte body 110. Vibration, shocks, and the like, to which the sensor may be exposed, particularly when installed in an automotive vehicle, are thus not transferred from the solid electrolyte body to any other unyielding, rigid element; thus, vibration and shock will not lead to electrical malfunction of the contacts, interruption of electrical continuity, or abrasion of conductive material.

The pre-stressed compression spring 24, bearing on one end against shoulder 23 of lug 20, bears with its other end against a connecting flange 40 of a metal sleeve, welded to, or otherwise secured to the connecting element 26", formed as a tube. The metal sleeve 40 bears against a washer 44 which preferably consists of a heat-resistant, plastically deformable substance such as asbestos, thinwalled, easily deformed metal rings, or other highly heat-resistant, yet yielding, resilient substances. The washer 44 presses against a yielding, resilient sealing mass 43 which, again, may be a metal, or other electrically conductive granulate. A washer 45, which may be similar to washer 44, fits against a shoulder 42, formed at the inside bore of the tube 110 formed, for example, by a counter-sunk recess at the upper end of the interior hollow portion 30 of the tube 110. The conductive strip or path 12 extends into the counter-sink opening of the tube 110, to make electrical contact with the mass 43 which, in turn, is in electrical contact with the sleeve 26″ and hence with the spring 24, to form a closed electrical circuit with the lug 20.

The mechanical, sealing, and electrical connection between the lug 20 and the outside of the sensor, and with the solid electrolyte tube thus is formed by a sealing assembly which includes three ring-shaped elements; the central ring 43 is formed of the electrically conductive, yielding resilient mass (for example graphite powder), and the two outer rings 44, 45 consist of a heat-resistant, plastically deformable substance such as asbestos, thin metal rings, or the like. The yielding, resilient connecting mass may also include electrically conductive material dispersed in a yielding, resilient binder.

The connection of the tube 10, or the tube 10′, 10″, 110, of FIGS. 1–4, respectively, to the outside housing 13 may, as shown in FIG. 4, include a resilient, yielding connection. Use of the compression spring 24 permits simultaneous connection and sealing, and electrical contacting between the solid electrolyte tube 10 and the housing 13, at the outside, as well as between the conductor 12 and the lug 20 at the inside of the solid electrolyte body. The solid electrolyte body 10 (10′, 10″, 110, respectively) is formed at its outside with an enlarged rim 46 (FIG. 4), defining a shoulder 47. Shoulder 47 bears against a yielding, resilient sealing connection generally shown at 48; the seal 48 corresponds to the seal of elements 43, 44, 45. The seal 48 fits against a shoulder 49 formed in the longitudinal bore of the housing 13 of the sensor. Spring 24 acts over the connecting portion 26″, the seal formed of elements 43, 44, 45, and the solid electrolyte tube 10, as well as by the seal 48, which is pressed on the shoulder 49 of housing 13. Thus, seal 48 includes two washers 44′, 45′, retaining therebetween a resilient, compressible sealing mass 43′.

Housing 13 is formed on its outside with a thread 51, and shaped with a polygonal surface, for example a hexagonal surface, to accept a hexagonal wrench, for assembly in a suitably tapped bore in the exhaust system of an internal combustion engine. The solid electrolyte tube 10 (10′, 10″, 110, respectively) is surrounded by a protective sleeve 53, formed with openings 54 to permit the passage of gas through the sleeve 53, and against the outer surface of the solid electrolyte tube. Sleeve 53 may be retained, for example, by an outwardly flared flange fitting against shoulder 49 of housing 13, and secured therein by the pressure of spring 24, acting over the seal 43–45, shoulder 43 on the solid electrolyte tube and then over the seal 48 against shoulder 49.

Various changes and modifications, may be made within the scope of the inventive concept and features described in connection with any embodiment may, likewise, be used with any other embodiment herein.

We claim:

1. Electro-chemical sensor construction having a tubular housing (13) with an opening therein (30);
   an ion conductive solid electrolyte tubular body (10, 110), closed at one end, and seated in the housing;
   an outer electrical conductor (11) located on the outer surface of the tubular body;
   an inner electrical conductor (12) located on the inner surface of the tubular body;
   a terminal (20) insulatingly secured to the housing (13, 15);
   an insulating disk (19) mechanically secured across the tubular housing (13, 15), the terminal (20) being attached to said disk and having a portion passing therethrough and facing the open end of the electrolyte body (19, 110);
   and a stressed helical compression spring (24) of electrically conductive material under compressive force extending axially within the housing, compressed between the tubular body (10, 110) and the terminal (20) forming at least a portion of the sole electrical connection between the terminal (20) and the inner conductor (12), as well as a mechanically reliable, yet resilient connection between the terminal and the tubular body (10, 110) on which the conductor (12) is located, the compressive force of the compression spring (24) being transferred to the housing (13, 15) by the tubular body (10, 110) and by the terminal (20) and the insulating disk (19).

2. Sensor construction according to claim 1, wherein the electrolyte body (10) has an end face (25), the inner conductor (12) extending at least in part over said end face;
   and a cap (26) is provided, fitting against said end face (25) and in electrical contact with said inner conductor (12), the compression spring (24) being in electrical and mechanical contact with said cap.

3. Sensor construction according to claim 2, wherein the end face (25) is substantially frusto-conical, the cap (26) has a conical surface matching the end face (25) and fitting thereover in contact with the inner conductor (12).

4. Sensor construction according to claim 1, wherein the end portion of the electrolyte body (10′) facing said compression spring is formed with a counter-sink of enlarged diameter with respect to the remainder of the tubular opening (30) in the body (10′) and defines a seating shoulder (32) at the inner end of the counter-sink (31);
   said inner conductor (12) extends to the counter-sink (31);
   and cup-shaped element (33) is provided fitting into counter-sink and bearing against said seating shoulder.

5. Sensor construction according to claim 4, wherein the cup-shaped element (33) is formed with an axial slit (35).

6. Sensor construction according to claim 1, wherein the end portion of the electrolyte body (10″) facing said compression spring is formed with a counter-sink (31) of enlarged diameter with respect to the remainder of the tubular opening (30) in the body (10″) and defines a seating shoulder (36) at the inner end of the counter-sink (31);
   said inner conductor (12″) extends to the counter-sink (31);
   and a sleeve-like element (26′) is provided having a diametrical enlargement (37), said enlargement fitting against the shoulder (36) of the countersink;

a resilient, compressible electrically conductive mass (38) located in the counter-sink surrounding said sleeve-like element adjacent the diametrical enlargement and in contact with said inner conductor;

and electrically conductive means (39) in engagement with said compression spring (24) and bearing against said resilient mass (38) to effect resilient, electrical connection between said inner conductor (12) and said spring (24).

7. Sensor construction according to claim 6, wherein said resilient mass is located at the side of the diametrical enlargement remote from the side bearing against said shoulder (36);

and said means (39) bearing against the resilient mass comprises a compression sleeve (39) surrounding said sleeve-like element and bearing on the resilient mass to compress the resilient mass between the diametrical enlargement of said sleeve-like element (26') and said bearing sleeve (39), said bearing sleeve being engaged by the compression spring (24).

8. Sensor construction according to claim 1, wherein the end portion of the electrolyte body (110) facing said compression spring is formed with a counter-sink (31) of enlarged diameter with respect to the remainder of the tubular opening (30) in the body (110) and defines a seating shoulder (42) at the inner end of the counter-sink (31);

said conductor (12) extends to the counter-sink (31);

and a tubular element (26'') is provided formed with a sleeve (40) at the end facing said spring (24), said spring bearing against said sleeve, and a resilient, yielding electrical sealing mass (43) compressed between said sleeve and the seating shoulder (42) and forming an electrical connection between the inner conductor (12) and the sleeve, against which the spring bears.

9. Sensor construction according to claim 8, further comprising radially extending retaining means (44, 45) extending from said tubular element (26'') spaced from each other and retaining said electrically conductive, resilient sealing mass therebetween.

10. Sensor construction according to claim 1, further comprising an elongated electrically conductive element (26') in mechanical, forcetransmitting relationship to said spring (24) and the tubular body (10);

a diametrical enlargement (37) extending from said elongated element, and a resilient, yielding sealing mass (38) of electrically conductive material located between said diametrical enlargement and the inner conductor (12) in contact with the inner surface of the tubular body (10'), to provide for resilient, yielding electrical connection between the elongated element and the inner conductor on the tubular body (10, 110).

11. Sensor construction according to claim 10, wherein the resilient sealing mass (38) is located within the internal hollow (30, 31) of the tubular body (10'') and comprises a granular electrically conductive substance including at least one of: graphite powder, graphite granules; pulverized copper.

12. Sensor according to claim 1, wherein the outer circumference of the solid electrolyte tube (110) is formed with a diametrical enlargement (46);

the housing (13) is formed with an inwardly extending shoulder (49), and a resilient, yielding electrically conductive sealing mass (48) located between the shoulder (49) formed in the housing and the shoulder (47) defined by the diametrical enlargement of the outside of the solid electrolyte tube, to provide for resilient, yielding seating of the electrolyte tube in the housing and electrical connection between the outer conductor (11) and the housing (13).

13. Sensor construction according to claim 12, wherein a protective tube (53) surrounds the solid electrolyte conductor, the protective tube having an outwardly flaring end, the outwardly flaring end seating against the shoulder (49) defined in the inside of the housing, and being resiliently retained thereby by the resilient electrically conductive mass (48), the retention force to said conductive mass being provided by the compression spring (24) bearing, over said connecting element (26; 26'', 40) against the solid electrolyte tube (110).

14. Sensor construction according to claim 1, wherein the housing for the sensor comprises two essentially tubular, axially aligned elements (13, 15) which are connected together, one of said elements (13) being formed with means (49) defining an inner shoulder, the ion conductive electrolyte tubular body (10, 110) seating against said shoulder, and the other element (15) having said insulating disk (19) to which the terminal (20) is attached and secured therein.

* * * * *